United States Patent [19]

Kamezawa et al.

[11] Patent Number: 4,975,508

[45] Date of Patent: Dec. 4, 1990

[54] ACRYLIC COPOLYMER ELASTOMERS

[75] Inventors: Mitsuhiro Kamezawa; Takao Hayashi, both of Yamaguchi, Japan

[73] Assignee: Tosoh Corporation, Yamaguchi, Japan

[21] Appl. No.: 269,392

[22] Filed: Nov. 10, 1988

[30] Foreign Application Priority Data

Nov. 10, 1987 [JP] Japan ................................ 62-282177

[51] Int. Cl.$^5$ ............................................. C08F 222/32
[52] U.S. Cl. .................................. 526/273; 526/292.6; 558/442
[58] Field of Search .................. 526/273, 292.6; 558/442

[56] References Cited

U.S. PATENT DOCUMENTS

| | | |
|---|---|---|
| 3,169,945 | 2/1965 | Hostettler et al. . |
| 3,201,373 | 8/1965 | Kaizerman et al. . |
| 3,312,677 | 4/1967 | Rosen . |
| 3,335,118 | 8/1967 | Kanavel et al. . |
| 3,458,461 | 7/1969 | Minal et al. . |
| 4,255,547 | 3/1981 | Arendt . |
| 4,625,005 | 11/1986 | Miyabayashi et al. ............ 526/292.6 |

FOREIGN PATENT DOCUMENTS 10893   8/1960   Japan .
1181509 2/1970  United Kingdom .

*Primary Examiner*—Bernard Lipman
*Attorney, Agent, or Firm*—Sughrue, Mion, Zinn, Macpeak & Seas

[57] ABSTRACT

An acrylic copolymer elastomer is disclosed, comprising (A) from 94.5 to 50% by weight of ethyl arcylate or ethyl arcylate containing not more than 50% by weight of n-butyl acrylate, (B) from 5 to 50% by weight of an arcylic acid ester and/or a methacrylic acid ester represented by formula (I):

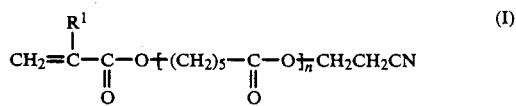

wherein the symbols are as defined in the appended claims, and (C) from 0.5 to 10% by weight of at least one of allyl glycidyl ether and glycidyl methacrylate, or vinyl chloroacetate, and having a Mooney viscosity (ML$_{1+4}$, 100° C.) of at least 10. This is a novel copolymer elastomer which is excellent in fuel resistance and low-temperature resistance.

7 Claims, No Drawings

ACRYLIC COPOLYMER ELASTOMERS

FIELD OF THE INVENTION

The present invention relates to novel acrylic copolymer elastomers, and more particularly to novel acrylic copolymer elastomers having excellent fuel resistance.

BACKGROUND OF THE INVENTION

Polymers of acrylic acid alkyl esters are known as acrylic rubbers. These acrylic rubbers are excellent in heat resistance and further in resistance against lubricant oil, and thus are widely used as an oil seal and so on. The acrylic rubbers, however, have no resistance against fuel oils having a lower aniline point than lubricating oils, such as gasoline, and thus they are applicable only to lubricating oils.

In order to improve the fuel resistance of acrylic rubbers, an attempt to use as a copolymerization component monomers having a functional group of high polarity, such as a cyano group and a fluorine-containing group, has been made. However, the introduction of such polar groups increases the glass transition point of the resulting copolymer and can provide only copolymer elastomers having poor low-temperature characteristics.

SUMMARY OF THE INVENTION

An object of the present invention is to provide acrylic elastomers which are improved in resistance against fuel oils without reducing their low-temperature characteristics.

It has been found that if acrylic acid esters having a specified structure are used as one component of monomers constituting acrylic elastomers, the fuel resistance is improved and the low-temperature characteristics are rather increased.

The present invention relates to an acrylic copolymer elastomer comprising:

(A) from 94.5 to 50% by weight of ethyl acrylate or ethyl acrylate containing not more than 50% by weight of n-butyl acrylate;

(B) from 5 to 50% by weight of an acrylic acid ester and/or a methacrylic acid ester represented by formula (I):

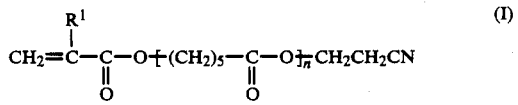

wherein $R^1$ is hydrogen or methyl group, and n is an integer of at least 1 and the number average value thereof is from 1 to 5; and (C) from 0.5 to 10% by weight of at least one of allyl glycidyl ether and glycidyl methacrylate, or vinyl chloroacetate, and having a Mooney viscosity ($ML_{1+4}(100°C.)$) of at least 10.

DETAILED DESCRIPTION OF THE INVENTION

The component (A) to be used in the present invention is ethyl acrylate or ethyl acrylate containing not more than 50% by weight of n-butyl acrylate. In the case of the mixture of ethyl acrylate and n-butyl acrylate, the proportion of n-butyl acrylate is not more than 50% by weight. If the proportion of n-butyl acrylate is more than 50% by weight, the fuel resistance is undesirably decreased.

The proportion of the component (A) in the monomer mixture is from 94.5 to 50% by weight. If the proportion of the component (A) is less than 50% by weight, only copolymer elastomers having decreased heat resistance and mechanical strength are obtained.

The component (B) to be used in the present invention is an acrylic acid ester and/or a methacrylic acid ester represented by formula (I). When the acrylic acid ester or methacrylic acid ester is produced by the usual method as described hereinafter, it is obtained as a mixture of those of formula (I) in which n is different. The mixture can be used as such. As a matter of course, acrylic acid esters or methacrylic acid esters having no molecular weight distribution as separated by techniques such as distillation can be used. In the present invention, the number average value of n is from 1 to 5. If the number average value of n is too large, the degree of unsaturation is lowered and polymerizability lowers, and furthermore the fuel resistance is less improved. The acrylic acid ester or methacrylic acid ester as the component (B) sometimes contains 2-cyanoethyl acrylate or 2-cyanoethyl methacrylate represented by formula (II):

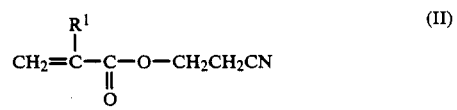

wherein $R^1$ is hydrogen or methyl group, owing to the process of production thereof. However no problem arises if the amount of 2-cyanoethyl acrylate or 2-cyanoethyl methacrylate is low as 20% by weight or less.

The acrylic acid ester or methacrylic acid ester as the component (B) can be easily prepared by the known process for preparation of acrylic acid esters in which a compound represented by (III):

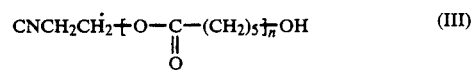

wherein n is an integer of at least 1 and the number average value thereof is from 1 to 5, is reacted with acrylic acid or methacrylic acid, or the known process for preparation of acrylic acid esters in which the compound of formula (III) and a halogenated acryloyl or a halogenated methacryloyl are reacted.

The compounds represented by formula (III) can be prepared by the known method in which ε-caprolactone is ring-opening added to ethylene cyanohydrin in the presence of a catalyst. Catalysts which can be used in the ring-opening addition reaction of ε-caprolactone includes organotitanium compounds such as tetraethoxytitanium and tetrabutoxytitanium; organotin compounds such as di-n-butyltin dilaurate and dibutyltin oxide; halogenated tin compounds such as stannous chloride; and perchloric acid. The amount of addition of ε-caprolactone in the above-described compound, i.e., the number average value of n, can be controlled by changing the molar ratio of ethylene cyanohydrin to ε-caprolactone.

The proportion of the component (B) in the monomer mixture is from 5 to 50% by weight and preferably from 10 to 40% by weight. If the proportion of the component (B) is too small, the effects of the present invention cannot be obtained. On the other hand, if it is too large, only copolymer elastomers having decreased thermal aging resistance and mechanical strength can be obtained.

The component (C) is a unit acting as a crosslinking site in the vulcanization of the copolymer elastomers of the present invention. More specifically, it is at least one of allyl glycidyl ether and glycidyl methacrylate, or vinyl chloroacetate. The proportion of the component (C) in the monomer mixture is from 0.5 to 10% by weight and preferably from 0.5 to 5% by weight. These cross-linking monomers can be used alone or as a mixture comprising two or more thereof. If the amount of the component (C) is too small, vulcanization proceeds only insufficiently. On the other hand, if it is too large, vulcanization proceeds excessively and no satisfactory vulcanized rubber sheet can be obtained.

The acrylic elastomers of the present invention can be easily produced by copolymerizing the above-described monomer mixture in the presence of a radical initiator by known copolymerization methods such as bulk polymerization, solution polymerization, emulsion polymerization, and suspension polymerization, with emulsion polymerization being particularly preferred.

Radical polymerization initiators which can be used include the usual radical initiators such as peroxides, redox compounds, persulfuric acid salts, and azo compounds.

Polymerization is carried out in the temperature range of from 0° to 100° C. and preferably from 5° to 80° C.

Copolymer elastomers obtained by polymerization can be easily isolated by salting-out using an aqueous solution of inorganic salts such as calcium chloride and sodium chloride, or by the use of a polymer-insoluble solvent such as methanol.

The Mooney viscosity ($ML_{1+4}(100°$ C.)) of the acrylic copolymer elastomer of the present invention is desirably at least 10 from the viewpoint of ease of molding, with the range of from 20 to 80 being preferred.

The acrylic copolymer elastomers of the present invention can be vulcanized by the same method as those commonly known for the vulcanization of acrylic rubbers.

By compounding a vulcanizing agent as chosen depending on the type of the component (C) acting as a cross-linking site into the copolymer elastomer and, if desired, further compounding a vulcanization accelerator, a reinforcing material, a filler, a plasticizer, an age-resistor, a stabilizer, and the like, the desired vulcanized rubber can be obtained. For example, in the case where the component (C) is vinyl chloroacetate, a combination of a metallic soap (e.g., sodium stearate and potassium stearate) and sulfur, a combination of the above-described metallic soap and pentamethylenethiuram polysulfide (TRA), and organic carboxylic acid ammonium salts (e.g., ammonium benzoate and ammonium adipate) can be used as the vulcanizing agent. In the case where the component (C) is at least one of glycidyl methacrylate and allyl glycidyl ether, carbamate compounds (e.g., hexamethylenediamine carbamate), ammonium benzoate, and polyamines can be used as the vulcanizing agent.

In accordance with the present invention, novel copolymer elastomers having excellent fuel resistance and low-temperature resistance can be obtained.

The present invention is described in greater detail with reference to the following examples.

PREPARATION EXAMPLE 1

383.4 parts by weight of ethylene cyanohydrin and 148.2 parts by weight of ε-caprolactone were placed in a three-necked flask equipped with a stirrer and a condenser, and then heated while stirring. When the temperature reached 150° C., 0.075 part by weight of tetrabutoxytitanium was added, and the reaction was performed in an atmosphere of nitrogen for about 5 hours while maintaining at 150° C. After the reaction, the conversions of ethylene cyanohydrin and ε-caprolactone were 8.9% and 98%, respectively. Unreacted ethylene cyanohydrin was removed from the reaction mixture by heating under reduced pressure to obtain a caprolactone adduct having a hydroxyl group at the terminal thereof. The average molecular weight of the caprolactone adduct as obtained above was 370. The conversions of ethylene cyanohydrin and ε-caprolactone were measured by gas chromatography, and the molecular weight of the caprolactone adduct was calculated from the KOH value as determined according to JIS K0070.

250 parts by weight of the caprolactone oligomer as obtained above, 65 parts by weight of acrylic acid, 500 parts by weight of toluene, 6.5 parts by weight of hydroquinone, and 3 parts by weight of sulfuric acid were placed in a flask equipped with a stirrer, a condenser and a separator and then were subjected to esterification reaction. Water formed by the reaction was distilled and condensed along with the solvent and removed from the flask by the use of the separator, and only the solvent was returned to the reaction system. At the point that the formation of water stopped, the reaction was terminated by cooling. The reaction mixture was neutralized with a 20% aqueous sodium hydroxide solution and washed several times with a 20% aqueous sodium chloride solution, and then the solvent was removed under reduced pressure to obtain the desired pale yellow acrylic acid ester. The molecular weights of the acrylic acid ester as determined by quantitative analysis of the terminal unsaturated group thereof and as calculated from the nitrogen content were shown in Table 1. The both were nearly in agreement with each other and thus it was confirmed that the desired acrylic acid ester was obtained. This was corresponding to a COmpound of formula (I) wherein $R^1$=H and the average value of n is 3.0. The 2-cyanoethyl acrylate content of the acrylic acid ester was not more than 1% by weight.

The quantitative analysis of the terminal unsaturated group was made by the morpholine method (method described in Kobunshi Gakkai, Koubunshi Jikkengaku Henshuiinkai edi., *Kobunshi Jikken Gaku*, Vol. 2, "Tanryoutai I", p. 225), and the nitrogen content was determined by elemental analysis. The 2-cyanoethyl acrylate content of the acrylic acid ester was quantitatively determined by gas chromatography.

PREPARATION EXAMPLE 2

A caprolactone adduct was prepared in the same manner as in Preparation Example 1 except that 355 parts by weight of ethylene cyanohydrin and 114 parts by weight of ε-caprolactone were used. After the reaction, the conversions of ethylene cyanohydrin and ε-caprolactone were 12.8% and 100%, respectively. The molecular weight of the caprolactone adduct obtained was 210. The esterification reaction was carried out in the same manner as in Preparation Example 1 except that 100 parts by weight of acrylic acid and 10 parts by weight of hydroquinone were used, to thereby obtain the desired acrylic acid ester. The molecular weights of the acrylic acid ester as determined from the terminal unsaturated group and as calculated from the nitrogen content in the same manner as in Preparation Example 1 are shown in Table 1. Since the both were nearly in agreement with each other, it was confirmed that the desired acrylic acid ester was formed. This was corresponding to the compound of formula (I) wherein $R^1$=H and the average value of n is 1.6. The 2-cyanoethyl acrylate content of the acrylic acid ester was not more than 1% by weight.

PREPARATION EXAMPLE 3

A caprolactone adduct was prepared in the same manner as in Preparation Example 2. After the reaction, the conversions of ethylene cyanohydrin and ε-caprolactone were 13.0% by weight and 99% by weight, respectively. The molecular weight of the resulting caprolactone adduct was 200. The esterification reaction was carried out in the same manner as in Preparation Example 2 to obtain the desired acrylic acid ester. The molecular weights of the acrylic acid ester as determined from the terminal unsaturated group and as calculated from the nitrogen content in the same manner as in Preparation Example 1 are shown in Table 1. Since the both were nearly in agreement with each other, it was confirmed that the desired acrylic acid ester was formed. This was corresponding to the compound of formula (I) wherein $R^1$=H and the number average value of n is 1.5. The 2-cyanoethyl acrylate content of the acrylic acid ester was 6% by weight.

PREPARATION EXAMPLE 4

A caprolactone adduct was prepared in the same manner as in Preparation Example 2. After the reaction, the conversions of ethylene cyanohydrin and ε-caprolactone were 12.5% and 100%, respectively. The molecular weight of the caprolactone adduct obtained was 215. The esterification reaction was carried out in the same manner as in Preparation Example 1 except that 125 parts by weight of methacrylic acid and 12.5 parts by weight of hydroquinone were used, to thereby obtain the desired methacrylic acid ester. The molecular weights of the methacrylic acid ester as determined from the terminal unsaturated group and as calculated from the nitrogen content in the same manner as in Example 1 are shown in Table 1. Since the both were nearly in agreement with each other, it was confirmed that the desired methacrylic acid ester was obtained. This was corresponding to the compound of formula (I) wherein $R^1$=$CH_3$ and the number average value of n is 1.6. The 2-cyanoethyl methacrylate content of the methacrylic acid ester was not more than 6% by weight.

EXAMPLES 1 TO 11 AND COMPARATIVE EXAMPLES 1 TO 5

One-fifth of a mixture of a monomer mixture having the formulation shown in Table 2 and n-dodecyl mercaptan (the amount was changed in order to modify the molecular weight) was mixed with an emulsion comprising 4 parts by weight of sodium dodecylbenzenesulfonate, 1 part by weight of sodium naphthalenesulfonate, 0.2 part by weight of tripotassium phosphate and 200 parts by weight of distilled water and emulsified by stirring. The temperature of the emulsion was adjusted to 10° C., and 0.01 part by weight of ferrous sulfate, 0.02 part by weight of trisodium ethylenediaminetetraacetate and 0.01 part by weight of paramenthane hydroperoxide were added to initiate the polymerization.

Then the remaining monomer mixture was dropped over about 6 hours while maintaining the temperature at 10° C., and at the same time, 0.05 part by weight of paramenthane hydroperoxide was added in divided portions. After the dropwise addition of the monomers was completed, polymerization was continued for 4 hours and then the reaction mixture was cooled to terminate the polymerization. The conversion of the monomers was 96 to 99%. The resulting copolymer latex was poured in an aqueous solution of sodium chloride maintained at 80° C. to isolate the copolymer which was then thoroughly washed with water and dried to obtain a copolymer elastomer. The composition of the copolymer thus obtained was shown in Table 3. The polymer composition was calculated from the nitrogen, chlorine and carbon contents of the polymer as determined by elemental analysis and the amount of unreacted monomers in the latex after the polymerization as determined by gas chromatography. The copolymer elastomers obtained in Examples 1 to 8 and Comparative Examples 1 to 2 were roll kneaded according to the formulation shown in Table 4 and then press vulcanized at 170° C. for 20 minutes to produce vulcanized rubber sheets. These sheets were heated at 150° C. for 4 hours in a gear oven and then measured for physical properties.

The copolymer elastomers obtained in Examples 9 to 11 and Comparative Examples 3 to 5 were roll kneaded according to the composition shown in Table 5 and then press vulcanized at 170° C. for 20 minutes to produce vulcanized rubber sheets. These sheets were heated at 150° C. for 4 hours in a gear oven and then measured for physical properties.

Physical properties of unvulcanized rubbers and vulcanized rubbers of Examples 1 to 10 and Comparative Examples 1 to 5 are shown in Table 6. The Mooney viscosity was measured according to JIS K6300, and the physical properties of vulcanized rubbers, according to JIS K6301. The fuel resistance was evaluated by dipping the vulcanized rubber in fuel oil C at 40° C. for 72 hours and measuring the change in volume. The glass transition temperature was measured using the unvulcanized rubber as a sample by means of a differential scanning calorimeter (DSC) at a heating rate of 10° C. per minute.

TABLE 1

| Preparation Example | Molecular Weight Calculated from Amount of Unsaturated Bond | Molecular Weight Calculated from Nitrogen Content |
|---|---|---|
| 1 | 460 | 467 |
| 2 | 309 | 318 |
| 3 | 294 | 297 |
| 4 | 322 | 333 |

TABLE 2

|  | Example |  |  |  |  |  |  |  | Comparative Example |  | Example |  |  | Comparative Example |  |  |
|---|---|---|---|---|---|---|---|---|---|---|---|---|---|---|---|---|
|  | 1 | 2 | 3 | 4 | 5 | 6 | 7 | 8 | 1 | 2 | 9 | 10 | 11 | 3 | 4 | 5 |
| Ethyl Acrylate | 77 | 67 | 57 | 67 | 67 | 67 | 47 | 67 | 97 | 67 | 69 | 49 | 65 | 99 | 69 | 95 |
| n-Butyl Acrylate | — | — | — | — | — | — | 20 | — | — | 30 | — | 20 | — | — | 30 | — |
| Acrylic Acid Ester of Preparation Example 1 | 20 | 30 | 40 | — | — | — | — | — | — | — | — | — | — | — | — | — |
| Acrylic Acid Ester of Preparation Example 2 | — | — | — | 30 | — | — | 30 | 25 | — | — | 30 | 30 | 30 | — | — | — |
| Acrylic Acid Ester of Preparation Example 3 | — | — | — | — | 30 | — | — | — | — | — | — | — | — | — | — | — |
| Methacrylic Acid Ester of Preparation Example 4 | — | — | — | — | — | 30 | — | 5 | — | — | — | — | — | — | — | — |
| Vinyl Chloroacetate | 3 | 3 | 3 | 3 | 3 | 3 | 3 | 3 | 3 | 3 | — | — | — | — | — | — |
| Glycidyl Methacrylate | — | — | — | — | — | — | — | — | — | — | 1 | 1 | — | 1 | 1 | — |
| Allyl Glycidyl Ether | — | — | — | — | — | — | — | — | — | — | — | — | 5 | — | — | 5 |

(unit: weight percent)

TABLE 3

|  | Example |  |  |  |  |  |  |  | Comparative Example |  | Example |  |  | Comparative Example |  |  |
|---|---|---|---|---|---|---|---|---|---|---|---|---|---|---|---|---|
|  | 1 | 2 | 3 | 4 | 5 | 6 | 7 | 8 | 1 | 2 | 9 | 10 | 11 | 3 | 4 | 5 |
| Ethyl Acrylate | 79.4 | 67.7 | 58.8 | 68.2 | 66.9 | 69.7 | 48.9 | 68.8 | 97.9 | 68.7 | 67.7 | 49.4 | 69.9 | 98.7 | 68.3 | 98.9 |
| n-Butyl Acrylate | — | — | — | — | — | — | 20.0 | — | — | 29.1 | — | 19.8 | — | — | 30.4 | — |
| Acrylic Acid Ester of Preparation Example 1 | 18.5 | 30.3 | 39.0 | — | — | — | — | — | — | — | — | — | — | — | — | — |
| Acrylic Acid Ester of Preparation Example 2 | — | — | — | 29.5 | — | — | 29.1 | 24.2 | — | — | 31.0 | 29.6 | 29.1 | — | — | — |
| Acrylic Acid Ester of Preparation Example 3 | — | — | — | — | 31.0 | — | — | — | — | — | — | — | — | — | — | — |
| Methacrylic Acid Ester of Preparation Example 4 | — | — | — | — | — | 28.3 | — | 4.8 | — | — | — | — | — | — | — | — |
| Vinyl Chloroacetate | 2.1 | 2.0 | 2.2 | 2.3 | 2.1 | 2.0 | 2.0 | 2.2 | 2.1 | 2.2 | — | — | — | — | — | — |
| Glycidyl Methacrylate | — | — | — | — | — | — | — | — | — | — | 1.3 | 1.2 | — | 1.3 | 1.3 | — |
| Allyl Glycidyl Ether | — | — | — | — | — | — | — | — | — | — | — | — | 1.0 | — | — | 1.1 |

(unit: weight percent)

TABLE 4

| | |
|---|---|
| Acrylic Copolymer Elastomer | 100 parts by weight |
| Stearic Acid | 1 parts by weight |
| Carbon Black MAF | 50 parts by weight |
| Sodium Stearate | 3 parts by weight |
| Potassium Stearate | 0.5 parts by weight |
| Sulfur | 0.3 parts by weight |

TABLE 5

| | |
|---|---|
| Acrylic Copolymer Elastomer | 100 parts by weight |
| Stearic Acid | 1 parts by weight |
| Carbon Black MAF | 50 parts by weight |
| Ammonium Benzoate | 1 parts by weight |

TABLE 6

|  | Example |  |  |  |  |  |  |  |
|---|---|---|---|---|---|---|---|---|
|  | 1 | 2 | 3 | 4 | 5 | 6 | 7 | 8 |
| Mooney Viscosity ($ML_{1+4}$, 100° C.) | 42 | 44 | 48 | 41 | 42 | 42 | 44 | 48 |
| Compound Mooney Viscosity ($ML_{1+4}$, 100° C.) | 80 | 83 | 85 | 80 | 77 | 81 | 80 | 86 |
| Physical Properties at Ordinary Temperature |  |  |  |  |  |  |  |  |
| Hardness (JIS-A) | 68 | 65 | 70 | 68 | 69 | 67 | 64 | 69 |
| Tensile Strength ($kg/cm^2$) | 145 | 136 | 127 | 140 | 138 | 125 | 120 | 125 |
| Elongation at Break (%) | 230 | 220 | 180 | 200 | 210 | 210 | 200 | 200 |
| 100% Modulus ($kg/cm^2$) | 55 | 57 | 58 | 53 | 52 | 53 | 50 | 53 |
| Fuel Resistance |  |  |  |  |  |  |  |  |
| Change in Volume after Dipping in Fuel Oil C at 40° C. for 72 Hours (%) | +69 | +57 | +49 | +48 | +45 | +50 | +61 | +50 |
| Low-Temperature Resistance |  |  |  |  |  |  |  |  |
| Glass Transition Temperature (°C.) | −28 | −34 | −37 | −32 | −31 | −28 | −35 | −31 |

|  | Comparative Example |  | Example |  |  | Comparative Example |  |  |
|---|---|---|---|---|---|---|---|---|
|  | 1 | 2 | 9 | 10 | 11 | 3 | 4 | 5 |
| Mooney Viscosity ($ML_{1+4}$, 100° C.) | 50 | 45 | 45 | 40 | 35 | 52 | 36 | 35 |
| Compound Mooney Viscosity ($ML_{1+4}$, 100° C.) | 73 | 68 | 80 | 77 | 64 | 66 | 51 | 60 |

TABLE 6-continued

| Physical Properties at Ordinary Temperature | | | | | | | | |
|---|---|---|---|---|---|---|---|---|
| Hardness (JIS-A) | 63 | 60 | 65 | 62 | 63 | 64 | 58 | 68 |
| Tensile Strength (kg/cm$^2$) | 145 | 119 | 125 | 118 | 130 | 158 | 125 | 122 |
| Elongation at Break (%) | 230 | 250 | 270 | 220 | 250 | 280 | 360 | 310 |
| 100% Modulus (kg/cm$^2$) | 46 | 45 | 49 | 53 | 53 | 41 | 42 | 38 |
| Fuel Resistance | | | | | | | | |
| Change in Volume after Dipping in Fuel Oil C at 40° C. for 72 Hours (%) | +108 | +144 | +47 | +59 | +48 | +105 | +142 | +110 |
| Low-Temperature Resistance | | | | | | | | |
| Glass Transition Temperature (°C.) | −17 | −35 | −31 | −36 | −32 | −17 | −35 | −18 |

While the invention has been described in detail and with reference to specific embodiments thereof, it will be apparent to one skilled in the art that various changes and modifications can be made therein without departing from the spirit and scope thereof.

What is claimed is:

1. An acrylic copolymer elastomer comprising:
   (A) from 94.5 to 50% by weight of ethyl acrylate or ethyl acrylate containing not more than 50% by weight of n-butyl acrylate based on component (A);
   (B) from 5 to 50% by weight of an acrylic acid ester and/or a methacrylic acid ester represented by formula (I):

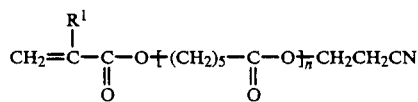

wherein R$^1$ is hydrogen or methyl group, and n is an integer of 1 or more and the number average value thereof is 1 to 5; and
   (C) from 0.5 to 10% by weight of at least one of allyl glycidyl ether and glycidyl methacrylate, or vinyl chloroacetate, and having a Mooney viscosity, ML$_{1+4}$ at 100° C. of at least 10.

2. An acrylic copolymer elastomer as in claim 1, wherein the component (B) is present in an amount of from 10 to 40% by weight of said elastomer.

3. An acrylic copolymer elastomer as in claim 1, wherein the component (C) is present in an amount of from 0.5 to 5% by weight of said elastomer.

4. An acrylic copolymer elastomer as in claim 1, having a Mooney viscosity, ML$_{1+4}$ at 100° C. of from 20 to 80.

5. An acrylic copolymer elastomer as in claim 1, wherein the component (B) contains 2-cyanoethyl acrylate or 2-cynoethyl methacrylate.

6. An acrylic copolymer elastomer as in claim 5, wherein said 2-cyanoethyl acrylate or 2-cyanoethyl methacrylate is present in an amount of not more than 20% by weight of the component (B) based on the entire polymer.

7. An acrylic acid ester and/or methacrylic acid ester represented by formula (I):

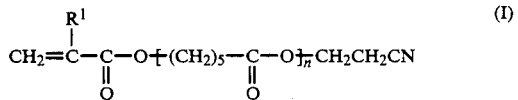

wherein R$^1$ is a hydrogen or methyl group, and n is an integer of 1 or more and the number average value thereof is 1 to 5.

* * * * *